(12) United States Patent
Reece (10) Patent No.: US 7,597,857 B2
(45) Date of Patent: Oct. 6, 2009

(54) APPARATUS TO BETTER DISTRIBUTE AN INSECT REPELLANT OR FRAGRANCE

(75) Inventor: Crale Reece, Townsville (AU)

(73) Assignee: Mozba Pty Ltd., Queensland (AU)

( * ) Notice: Subject to any disclaimer, the term of this patent is extended or adjusted under 35 U.S.C. 154(b) by 0 days.

(21) Appl. No.: 11/979,754

(22) Filed: Nov. 8, 2007

(65) Prior Publication Data

US 2008/0178518 A1    Jul. 31, 2008

Related U.S. Application Data

(63) Continuation of application No. 10/523,973, filed on Feb. 8, 2005, now abandoned.

(30) Foreign Application Priority Data

| Aug. 9, 2002 | (AU) | ................................ 2002300482 |
| Nov. 26, 2002 | (AU) | ................................ 2002304031 |
| Aug. 5, 2003 | (WO) | ................ PCT/AU2003/000986 |

(51) Int. Cl.
| A61L 9/015 | (2006.01) |
| A61L 9/03 | (2006.01) |
| A61L 9/04 | (2006.01) |
| A61L 9/12 | (2006.01) |

(52) U.S. Cl. ..................... 422/124; 422/125; 422/126

(58) Field of Classification Search ....................... None
See application file for complete search history.

(56) References Cited

U.S. PATENT DOCUMENTS

| 3,990,848 | A | 11/1976 | Corris |
| 4,601,886 | A | 7/1986 | Hudgins |
| 5,141,706 | A | 8/1992 | Clark |
| 5,567,361 | A | 10/1996 | Harper |
| 5,833,929 | A | 11/1998 | Watson et al. |
| 5,993,748 | A * | 11/1999 | Wheeler ..................... 422/125 |
| 6,032,930 | A | 3/2000 | Calino |

FOREIGN PATENT DOCUMENTS

| GB |  | 2222775 | 3/1990 |
| WO | WO | 88/08721 | 11/1988 |
| WO | WO | 00/69479 | 11/2000 |

* cited by examiner

*Primary Examiner*—Elizabeth L McKane
(74) *Attorney, Agent, or Firm*—Hoffman, Wasson & Gitler, P.C.

(57) ABSTRACT

A fan containing apparatus has a first enclosure which can accommodate a conventional mosquito coil/mosquito candle/vaporizing device, etc. The smoke/vapors are blown by the fan through an outlet in the apparatus to provide a much better distribution of the gas/smoke/vapor into a room. A perforated hose can be attached to the outlet to provide a much better positioning of the gas/smoke/vapor in a room or outdoor area.

18 Claims, 5 Drawing Sheets

APPARATUS TO BETTER DISTRIBUTE AN INSECT REPELLANT OR FRAGRANCE

This application is a continuation of Ser. No. 10/523,973, filed on Feb. 8, 2005, now abandoned.

FIELD OF THE INVENTION

This invention is directed to an apparatus (typically in the form of a small box) which can better distribute the smoke from a mosquito coil/candle etc or which can better distribute the vapor from a vaporizer. In a broad form, the invention is directed to a fan containing apparatus which can better distribute any type of beneficial vapor/smoke/gas etc. The beneficial action may comprise an insect repellent, a fragrance, a deodorizing agent and the like.

BACKGROUND ART

A very common way to deter or repel mosquitoes and biting insects is to place a mosquito coil or a mosquito candle in the area where the deterrent effect is required. The smoke from the mosquito coil and the vapor from the mosquito candle provides a deterrent to biting insects. A disadvantage with these coils and candles is that the effective deterrent area is not very large. If the mosquito coil or candle is placed in a closed room, it is found that the greatest deterrent occurs above the coil or candle as the smoke/vapors tend to move upwardly. Conversely, if the mosquito coil or candle is placed outside, a breeze will tend to blow the smoke/vapor away from the deterrent area.

With mosquitoes, it is noticed that mosquitoes tend to congregate in certain areas. In a room, it is noticed that mosquitoes tend to congregate about the corners of the room. However, the smoke from the mosquito coil or the vapor from a mosquito candle does not effectively extend into this area.

Many types of vaporizing devices are known. One common type of vaporizing device is electrically operated and can be plugged into a power socket. The device contains a small reservoir of liquid repellent/fragrance/deodorizing agent etc and contains a small heating device which heats the liquid or a proportion of liquid. Again, a disadvantage with this device is that the treatment area is not very large. To properly deodorize an entire room, or to provide a repelling action in an entire room, it takes a long time before the vapors/smoke extends throughout the room.

It will be clearly understood that, if a prior art publication is referred to herein, this reference does not constitute an admission that the publication forms part of the common general knowledge in the art in Australia or in any other country.

OBJECT OF THE INVENTION

The present invention is directed to a simple yet extremely useful device or apparatus which can assist in dispersing the smoke from a mosquito coil, the vapor from a mosquito candle, the vapor from a vaporizer etc in a more efficient manner.

It is an object of the invention to provide an apparatus which may overcome at least some of the above-mentioned disadvantages and/or provide the public with a useful or commercial choice.

In one form, the invention resides in an apparatus to dispense a beneficial gas/smoke/vapor, the apparatus having an enclosure, the enclosure adapted to contain a gas/smoke/vapor generating device, a fan to pass air at least partially through the enclosure and to entrain at least some of the gas/smoke/vapor, an outlet through which the gas/smoke/vapor can pass.

The term "beneficial gas/smoke vapor" includes the smoke from a mosquito coil, vapors from a vaporizing device such as a candle, an electrically operated vaporizer, and other devices that generate a smoke/gas/vapor that repels, kills or otherwise deters insects, moths and other undesirable creatures.

It is preferred that an elongate tube is provided, and that the tube has at least one opening which is operatively associated with the outlet such that gas/smoke/vapor passing through the outlet passes at least partially through the tube. The tube may have a length of between 1-10 m or even more, and may have a diameter of between 5-50 mm or even more. The tube may be perforated at least partially along its length and therefore make comprise a perforated ducting. Preferably, the tube is perforated along its length which allows the smoke/gas/vapor to pass out of the perforations. The tube may comprise a tube having sections which are not perforated and sections which are perforated. The smoke/gas/vapor will pass along the non perforated section of the tube and through the openings in the perforated section of the tube. This allows the tube to be laid in such a manner that the smoke/gas/vapor only passes into a desired area. This can be achieved, if necessary, by providing separate tubes which can be fitted together with one tube not been perforated and another tube being perforated. This concept can be extended to include tube lengths having different types, sizes and numbers of perforations to control the volume of smoke/gas/vapor passing out of the tube at any particular place.

The tube, or perforated ducting, can be made of any suitable material which may include plastics. The tube is preferably sufficiently flexible to allow it to be placed in desired areas. Alternatively, the tube may be at least partially rigid, particularly where the tube forms part of a fixed system, as opposed to a portable system for the dispersion of the smoke/gas/vapor. Such a fixed system may be installed about a building for example.

The tube may have closeable openings to provide versatility to the device. This can be in the form of a collar which is slidable over the tube and which can close off some openings. Valves, taps and the like can also be present to direct the smoke to desired parts of the tube.

The tube may be substantially circular if desired although this is not necessary. Alternatively, the tube may be rectangular, oval, or have other shapes. It is considered that the tube may have a discreet or "low-profile" and this can be achieved by giving the tube a flattened oval shape, or giving the tube a rectangular shape having a low-profile.

The tube may be positioned along the ground to enable the smoke etc to be directed into a suitable region. In one form, the tube may be simply laid along the ground. However, the tube may also be suspended from a wall, post, or anchored to the ground or otherwise placed in position. Thus, the invention may also comprise fasteners, attachment, clips, or other types of accessories to enable the tube to be placed in a desired position. These fasteners etc may be separate and the tube may be attached to the fasteners; alternatively, the fasteners may comprise part of the tube or may be otherwise attached to the tube.

Suitably, the fan passes air from outside the enclosure and into the enclosure. In this manner, the smoke laden air does not pass through the fan. However, in another form, the fan may form part of a fan enclosure which has an inlet and an outlet, the inlet of the fan enclosure being in communication with the enclosure, and the outlet of the fan enclosure being in communication with the outside of the apparatus. In this version of the invention, the smoke laden air does pass through the fan.

In another form, the invention resides in an apparatus, the apparatus having a first enclosure adapted to contain a mosquito coil/candle/vaporizing device, an inlet to allow air to pass into the first enclosure, a fan enclosure which has an inlet and an outlet, a fan, the inlet of the fan enclosure being in communication with the first enclosure, and the outlet of the fan enclosure being in communication with the outside of the apparatus.

Thus, in accordance with the invention, a commercially available mosquito coil or mosquito candle can be lit and placed in the enclosure. The fan can then be started which will blow the smoke containing air more vigorously into a room/outside area etc. There is no need to provide a complicated system to produce the smoke/vapor as the apparatus allows a conventional mosquito coil, mosquito candle etc to be used.

In an extremely broad form, the invention can comprise an apparatus having a single enclosure in which the mosquito coil etc can be placed. A fan can blow air through the enclosure and through an outlet to direct smoke laden air to a desired area. The fan can be placed in the enclosure, next to the enclosure etc. The fan can be reversed such that the air can be sucked through the enclosure from the outlet and through the inlet. Other changes and modifications are envisaged.

The apparatus is typically box shaped in configuration and small enough to be placed on the ground, on a shelf, on a stand etc. However, there is no need for the apparatus to be box shaped and other types of shapes are envisaged. However, the apparatus will typically have a top wall, a bottom wall, a rear-wall, sidewalls and a front wall. The enclosure should be large enough to accommodate the mosquito coil etc which is to be placed in the enclosure. The size of this can vary to suit.

The enclosure typically has an air inlet to allow air to pass into the enclosure. The air inlet may comprise a series of perforations in one or more walls of the enclosure, although other arrangements are envisaged.

The enclosure is typically provided with some form of door/flap or other type of access means to allow the mosquito coil etc to be placed into the first enclosure. Typically, a side wall of the apparatus may be hinged to provide a door. However, it is preferred that a portion of one side wall is removable from the enclosure. This allows the apparatus to be simple in design.

It is preferred that the air inlet comprises one or more apertures in the door. Thus, the door can be seen as a vented door. However, the air inlet may be another part of the apparatus. For instance, if the fan draws air from the outside of the enclosure, the air inlet may comprise the inlet of the fan.

It is preferred that the enclosure is made of heat resistant material. This minimizes any chance of damage to the first enclosure by virtue of a mosquito candle, a lit mosquito coil etc.

In one embodiment of the invention, the apparatus may comprise a pressurized unit. In this version, the fan may have an inlet communicating with the outside of the enclosure, and an outlet communicating with the inside of the enclosure. Thus, air is blown into the inside of the enclosure causing a degree of pressurization. The enclosure may comprise an outlet through which the pressurized air can pass. The outlet may be attached to or otherwise in communication with a perforated ducting as described above. Suitably, the mosquito coil/candle/vaporizing device etc is positioned in the enclosure.

In another embodiment of the invention, the apparatus is provided with a venturi. The venturi may comprise a tube in the enclosure. One end of the tube is associated with the fan outlet such that pressurized air blows from the fan outlet and into the venturi. The other end of the venturi can be associated with the outlet. As the air blows into the venturi, it provides a region of low-pressure which sucks in adjacent air. The adjacent air comprises the smoke/gas/vapor laden air in the enclosure. An advantage of this arrangement is that smoke does not pass through the fan.

The apparatus may have a fan enclosure. The fan enclosure typically comprises a shroud about a fan, the shroud having an inlet and an outlet. Other types of arrangements are envisaged however it is preferred that the design of the fan and fan enclosure is such that there is little mixing of incoming air and exiting air as the function of the fan is to blow the smoke/vapor laden air out of the apparatus. The fan enclosure may be formed in a second enclosure of the apparatus. The second enclosure may be separated from the first enclosure and this can be achieved using a partition wall and the like. This arrangement can prevent damage to the fan. The inlet of the fan enclosure may be in communication with the first enclosure. Typically, the fan enclosure is attached to one wall of the first enclosure, and an opening is provided in the wall to allow air to pass into the inlet of the fan enclosure. If desired, a screen, filter etc may be provided. The outlet of the fan enclosure can communicate with the outside of the apparatus. In a simple form the outlet may communicate with or be part of a tube, conduit, or other type of enclosure which funnels the air passing through the outlet towards an outlet in the apparatus.

The outlet in the apparatus may comprise a valve or other type of opening. The advantage of this arrangement is that a flexible hose can be attached to the outlet. The hose may be perforated and blocked at the end to force the mosquito coil smoke etc to pass through the perforations in the hose. The hose may be several meters long and may be placed wherever necessary in a room or an outdoor area to provide a much greater repellent action than would be possible with a single mosquito coil or even a number of mosquito coils. Thus, one advantage of the apparatus is that a single mosquito coil/mosquito candle can be as effective in a larger area which previously would require a large number of candles/coils etc. Moreover, by using the flexible hose the repellent smoke/vapor etc can be channeled to precisely where needed.

Alternatively, the apparatus may be provided with a second enclosure/third enclosure and like which may be provided with an open top, an elongate slot etc to allow smoke/vapor to pass from the apparatus. While this arrangement does not contain a flexible hose, it will still disperse the smoke/vapor more efficiently.

The fan may be electrically powered. In one form of the invention, the fan may be powered by a battery. In another form of the invention, the fan may be powered by a rechargeable battery and the battery can be recharged from a power source using conventional techniques. In another form, the fan may be powered from a vehicle cigarette lighter socket, or mains power. It is envisaged that the fan may also be solar powered. It is envisaged that the fan may be a variable speed fan and some form of control knob etc can be provided to adjust the rotational speed of the fan. The fan may be controlled by an on/off switch or by any other suitable means.

The apparatus need not be limited to use with a mosquito coil, mosquito candle, an oil or any other product which is lit or burnt to provide the repellent action. For instance, the apparatus is sufficiently versatile to enable it to be used with a vaporizing device. A typical well-known vaporizing device plugs into a power socket. Therefore, the apparatus may be provided with a power socket in the first enclosure to enable a conventional vaporizing device to be simply plugged into the socket in the first enclosure.

According to an alternative embodiment, the invention resides in an apparatus to dispense a beneficial gas/smoke/vapor, the apparatus having a housing with at least one opening therein, the housing containing a gas/smoke/vapor generating device, a fan located in the housing to pass air at least partially through the enclosure and to entrain at least some of the gas/smoke/vapor, and an outlet through which the gas/smoke/vapor can pass.

As with the previous embodiments, it is preferred that an elongate perforated tube is provided, and that the tube has at least one opening which is operatively associated with the outlet such that gas/smoke/vapor passing through the outlet passes at least partially through the tube.

The housing is typically connected to a power source and provided with a control system to control the gas/smoke/vapor generating device and the fan. Typically, the control system is provided internally within the housing, with a control panel on the exterior of the housing with which to adjust and/or program the control system.

The housing is typically an enclosure having a plurality of breather openings in at least one side wall in order to draw in air from outside the enclosure with which to entrain the gas/smoke/vapor within the enclosure. Locating the fan within the enclosure forms a pressure differential between the interior of the enclosure and the exterior of the enclosure with the fan directing the gas/smoke/vapor and air into the outlet and perforated tube, thus preventing or minimizing the amount of gas/smoke/vapor which can escape through the breather openings in the housing.

Typically, the gas/smoke/vapor generating device includes a reservoir with a vaporizing means associated therewith. Normally, the reservoir and vaporizer will be a substantially closed unit with a minimal number of openings. Therefore, the device of the present invention will have the preferred configuration of a substantially closed reservoir located within the substantially enclosed housing.

Preferably, the vaporizing means is provided with an outlet which is located adjacent the fan. Thus, in use the vaporized material (gas/smoke/vapor) will either will disperse within the housing and be entrained by the air drawn in through the breather openings when the fan is operational or the air drawn into the housing by the fan will more directly entrain the vaporized material as both flow towards the fan.

In a particularly preferred embodiment, the vaporizing means may be provided as the lid (cap or closure) for the reservoir.

It is particularly preferred that the fan is provided with a fan housing again with the fan housing located with in the housing of the device. In the fan housing preferably includes at least two portions, namely a first annular portion in which the fan itself is located and a second in directing portion which communicates with the annular portion and links the annular portion with the outlet from the housing. It is preferred that the hand and fan housing are located on a rear wall of the housing, preferably above and slightly behind the reservoir. As the material within the reservoir is converted into gas/smoke/vapor, the gaseous material will normally rise, and thereby be entrained by the air entering through the breather openings in the housing.

According to a particularly preferred embodiment, the vaporizing means is spaced from the lower wall of the housing with the breather openings located at a similar level to the vaporizing means to promote the proper flow of air (and air entrained gas/smoke/vapor) to the outlet.

A portion of one side wall is removable from the enclosure to allow removal and replacement of the vaporizing means.

BRIEF DESCRIPTION OF THE DRAWINGS

Embodiments of the invention will be described with reference to the following drawings in which.

DETAILED DESCRIPTION OF THE INVENTION

Figure 1:
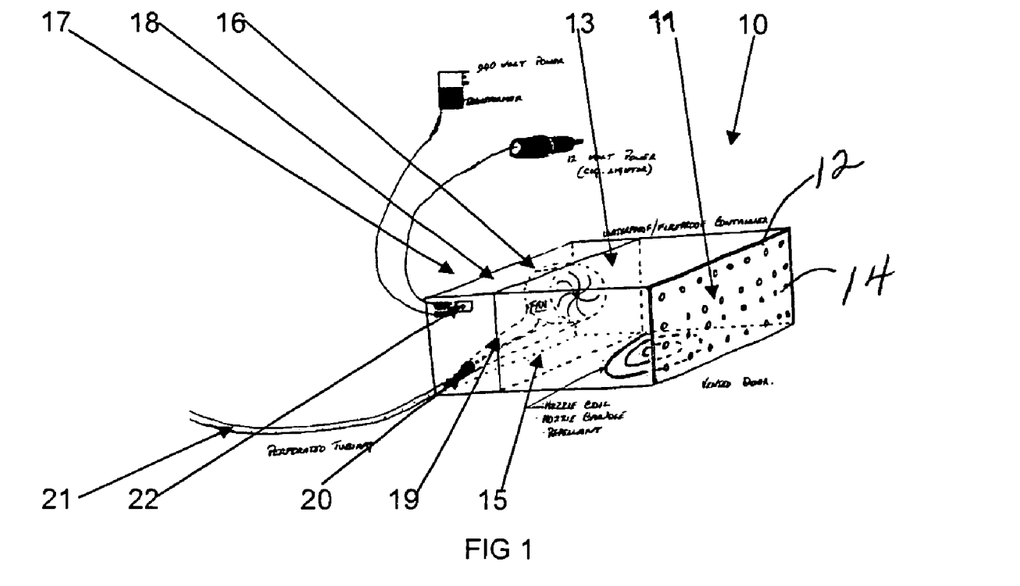
FIG. 1 illustrates an apparatus for use with a mosquito coil/mosquito candle etc.

Referring to the drawings and initially to FIG. 1 there is illustrated an apparatus 10 which can better disperse a repellent/fragrance/deodorizing composition etc in a particular area. The apparatus 10 is substantially box like and can have a length of between 20-60 cm, a width of between 10-40 cm and a height of between 10-30 cm. These dimensions can of course vary to suit. The apparatus can be made of any suitable material but it is preferred that the material is substantially waterproof (to allow the apparatus to be used outdoors) and fireproof (to allow a mosquito candle etc. to be placed in the apparatus). Thus, the material may comprise metal, fiber cement and the like.

The apparatus has a top wall, a bottom wall, a rear wall, a pair of closed sidewalls, and a front wall, these walls being substantially continuous and attached to form a substantially enclosed container. However, the front wall comprises a door 11. Door 11 is hinged at the top by a horizontal hinge 12 which allows the door to naturally fall into a closed position allowing the door to have a very simple yet effective design. However, the door can also be hinged by a bottom hinge, a side hinge, can be a sliding door, a clip on door or any other type of door.

The door forms one side of a first enclosure 13. The first enclosure 13 is large enough to hold a mosquito coil/mosquito candle or any other device which is to be placed within the first enclosure. The first enclosure is defined by part of the top wall, part of the bottom wall, and part of each side wall as well as the door 11. In the particular embodiment, the rear wall does not form part of the first enclosure. Door 11 is provided with an array of vent openings 14 to allow air to pass into the first enclosure. While this is a simple arrangement, the invention is not to be limited to this particular type of air inlet to the first enclosure.

The first enclosure 13 is also defined by an intermediate partition wall 15. Wall 15 is provided with an opening which forms part of the inlet to the fan enclosure 16. The partition wall 15 is spaced from rear wall 17 to form a second area 18 which is separated from the first enclosure 13.

The second area 18 contains the fan enclosure 16. The fan enclosure 16 is a cylindrical shroud which passes about the fan. The enclosure 16 has a fan inlet which extends into the first enclosure 13, and a fan outlet which comprises a tapering tube 19 which tapers to an outlet 20 passing through a side wall of the container. The outlet 20 allows a flexible perforated hose 21 to be attached to the outlet. The hose 21 can have any suitable length and diameter and allows the exhaust from the fan (containing the mosquito smoke etc) to be dispersed to any suitable area simply by positioning the perforated hose in that area. This provides a real and substantial advantage over other devices.

The fan can be powered either by a 12 volt power source (typically a vehicle cigarette lighter) or by a transformer to transform mains power into a lower voltage. In the embodiment, a power socket 22 is provided on one side wall into which the cigarette lighter attachment can plug or into which the transformer can plug, providing versatility to the apparatus.

When camping, the apparatus can be placed next to a campsite and can be powered by the cigarette lighter attachment in a vehicle. The flexible hose 21 can be positioned around the area which is to be protected. In a house, the apparatus can be placed on the ground or anywhere else and the flexible hose can be placed against the wall of the room as an extremely efficient and effective deterrent. It is also found that use of the fan provides better burning of a mosquito coil by providing a continual draft of air to assist in the burning action. This again adds to the efficiency of the apparatus.

Figure 2:
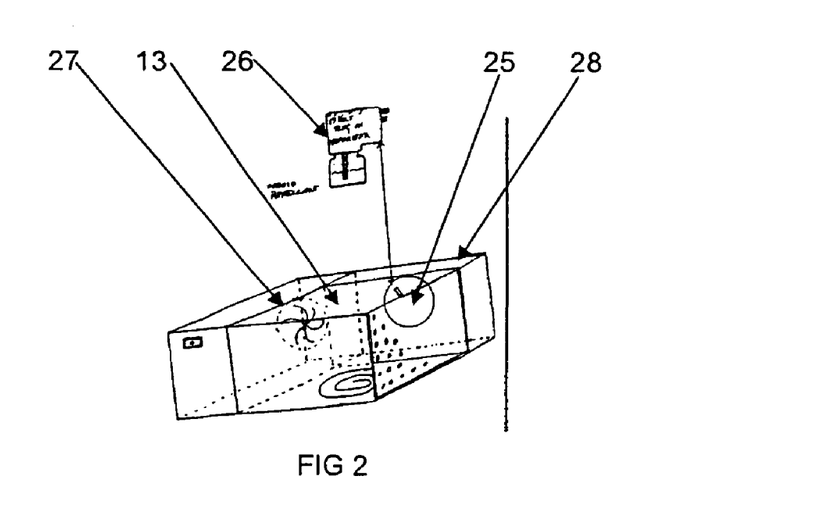
FIG. 2 illustrates an apparatus for use with a plug in vaporizer.

Referring to FIG. 2, there is described an apparatus which is similar to the apparatus of FIG. 1 except that one wall of the first enclosure 13 is provided with a socket 25 to enable a plug in vaporizer 26 to be simply plugged into the socket 25 inside enclosure 13. A fan 27 can then be operated to suck air through the first enclosure in a manner similar to that described above. In this arrangement and other compartment 28 is provided. This compartment can contain the rear portion of socket 25 and can be electrically insulated from the remainder of the container.

Figure 3:
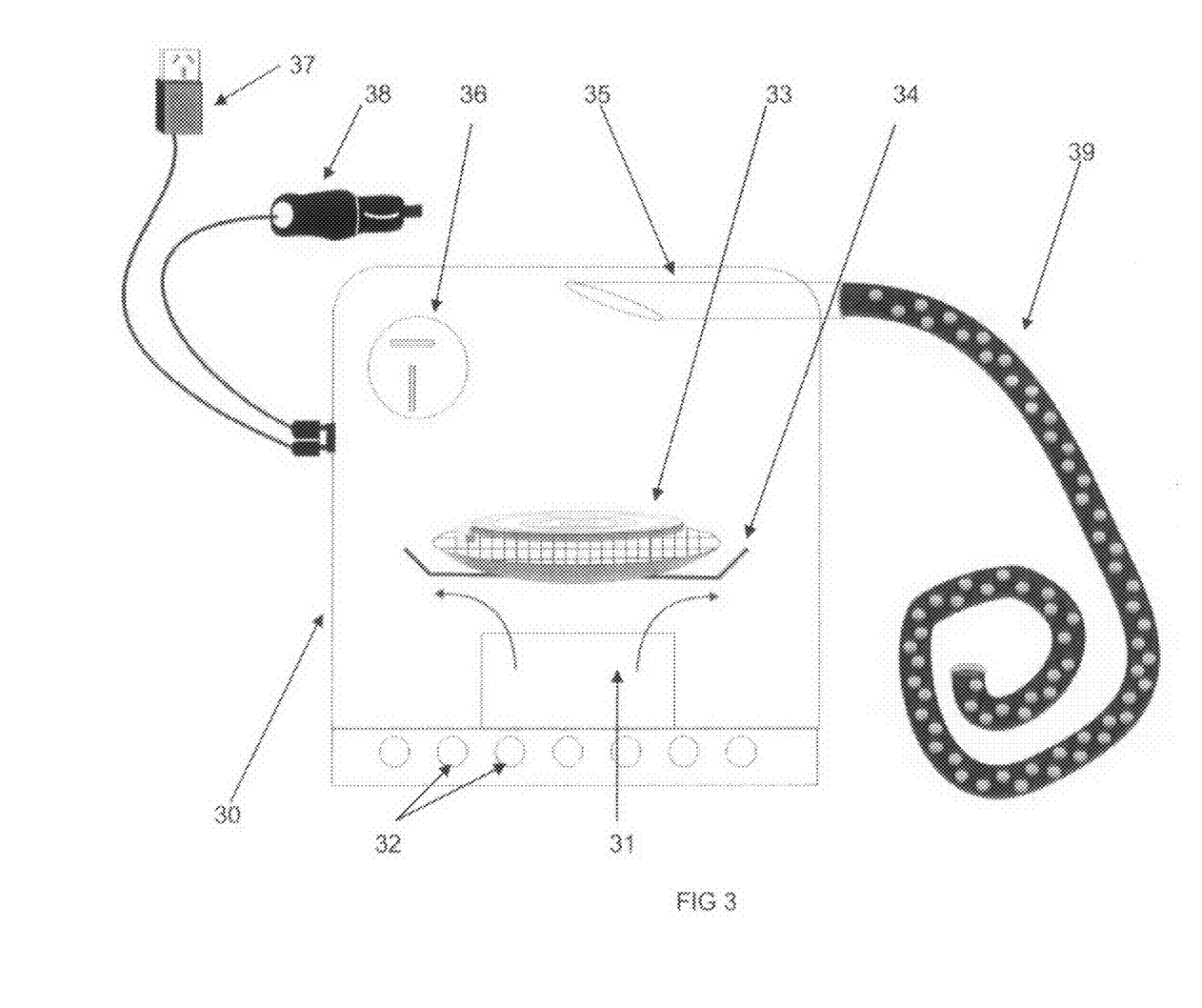
FIG. 3 illustrates a further embodiment of the apparatus in the form of a pressurized unit.

Referring to FIG. 3, there is illustrated a pressurized unit. One advantage of this unit is that the smoke laden air does not pass through the fan. The unit comprises a box like housing 30. At the bottom of the housing is a fan 31. The fan 31 draws air into housing 30 through a number of air inlet openings 32. The openings 32 communicate with the outside of housing 30. A mosquito coil/candle/repellent 33 is positioned above fan 31. This material is placed in a tray 34. The tray is made of solid material and is positioned above fan 31. As the fan blows air against the bottom of tray 34, the air passes around the sides of the tray and towards outlet 35. During this process, the smoke from the mosquito coil etc will be mixed with the air such that smoke laden air will pass through outlet 35. Tray 34 prevents the coil etc from burning too quickly by preventing air from blowing directly against the coil. The unit can also contain a vaporizing device (not illustrated) which can be plugged into plug 36 and this can be connected to a source of electrical power in a manner already described above, which may include mains power via a transformer 37, or battery power via a cigarette lighter socket 38. Of course, other types of power sources are envisaged such as solar power etc. The outlet 35 communicates with the perforated ducting 391 already described above, which allows the smoke laden air to be dispensed in any desirable place.

Figure 4:
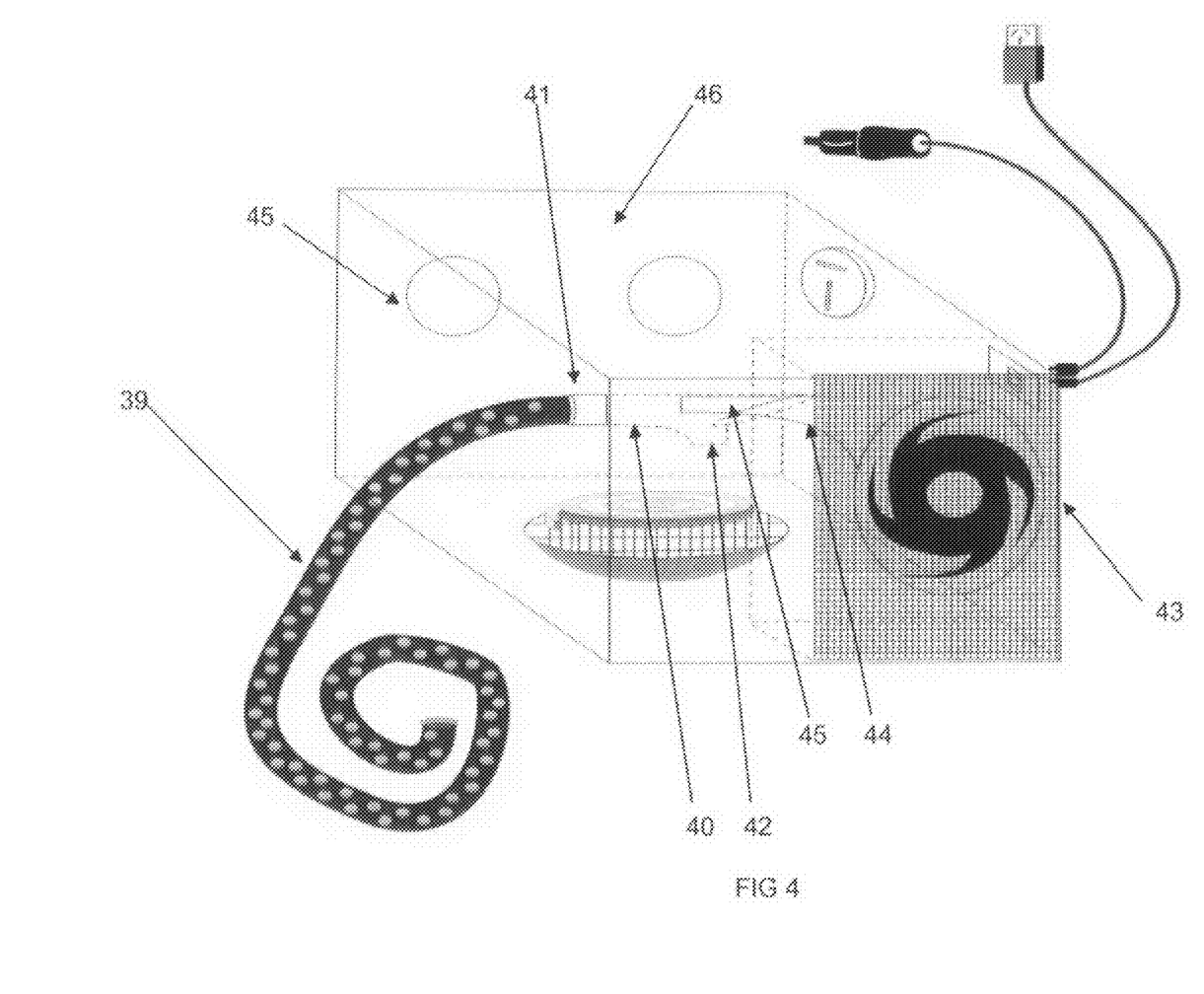
FIG. 4 illustrates a further embodiment of the apparatus containing a venture.

FIG. 4 illustrates another variation which again has the benefit of preventing smoke laden air passing through the fan. This variation can be seen as the "venturi variation". In this variation, a venturi pipe 40 is provided, one end of which forms the outlet 41. The perforated ducting 39 is connected to outlet 41 in a manner similar to that described above. The other end of the venturi has a flared opening 42. The fan 43 draws air in from the outside of the unit and through a fan housing 44 which has a nozzle like outlet 45 which blows pressurized air into the flared opening 42. By doing so, an area of low-pressure is created which sucks adjacent air through venturi 40. The adjacent air is the smoke/vapor laden air inside the unit. The unit contains the mosquito coil/candle or a vaporizing device similar to that described above. An advantage of this arrangement is that the unit is not pressurized. Further inlet openings 45 are provided in the vented door 46 to replace air which passes through the venturi by virtue of the "venturi effect".

Figure 5:
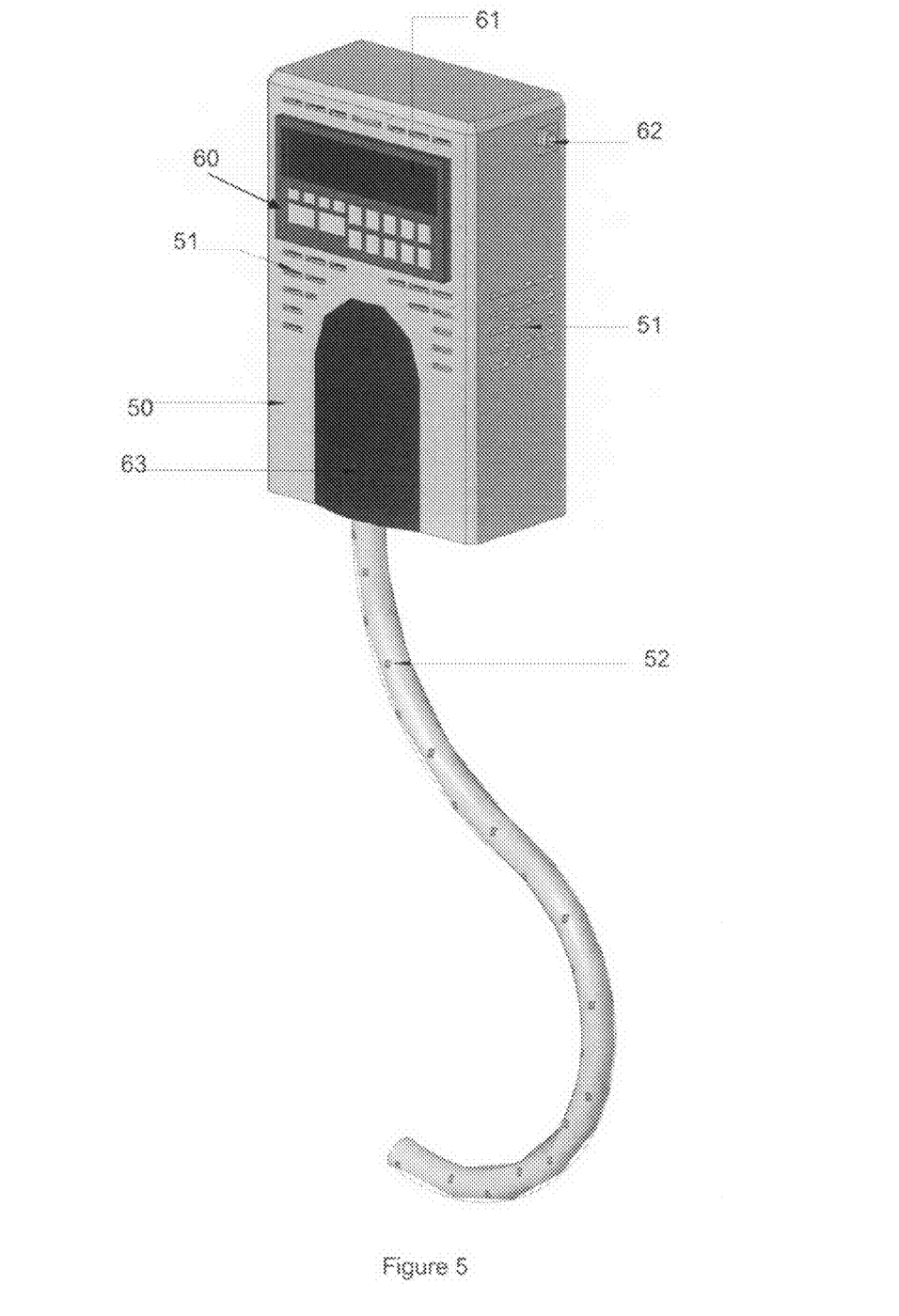
FIG. 5 illustrates a perspective view of an apparatus for distributing an insect repellant according to a further embodiment.
Figure 6:
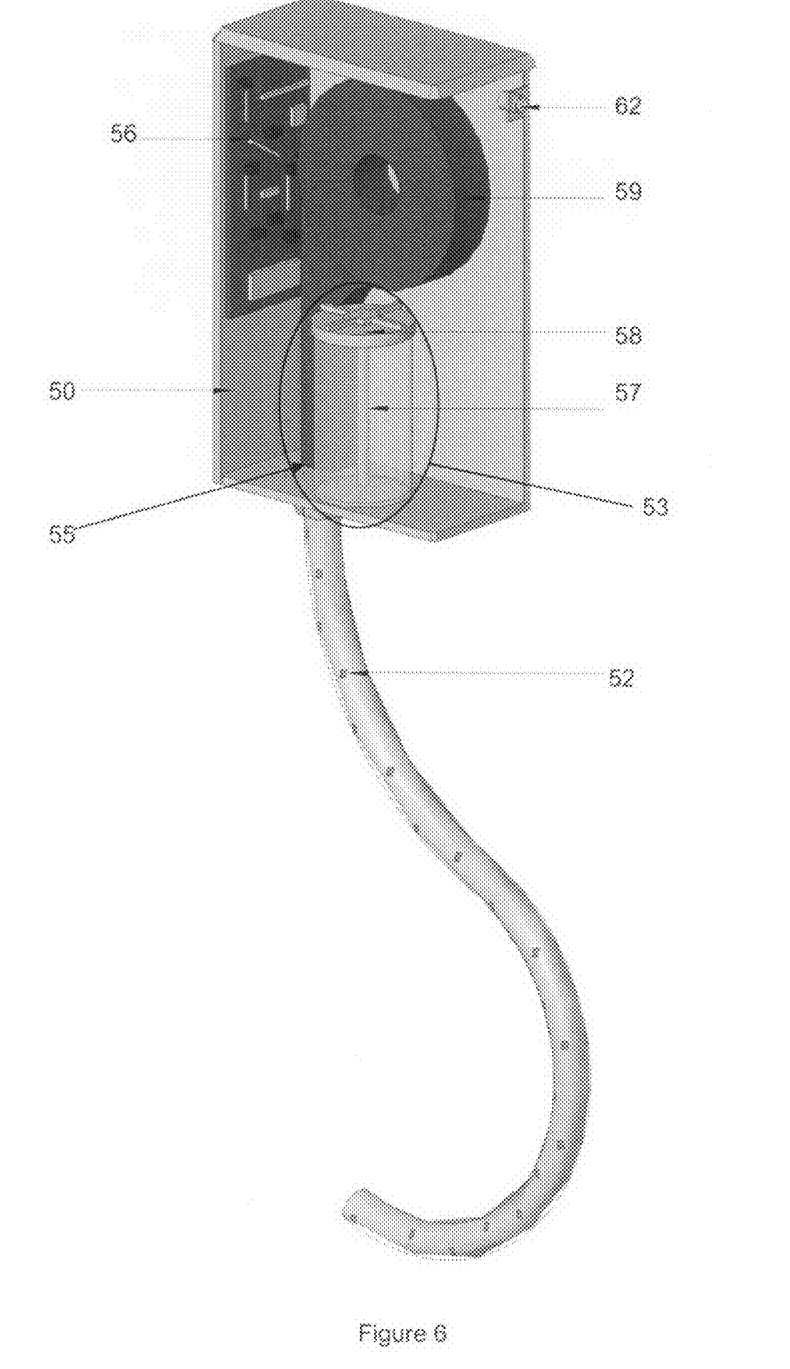
FIG. 6 illustrates a cutaway view of an apparatus for distributing an insect repellant according to the embodiment illustrated in FIG. 5.

The apparatus may have an alternative configuration according to an alternative embodiment as illustrated in FIGS. 5 and 6. The apparatus illustrated in these Figures has an external housing 50 in which all components except the perforated tube 52 are contained. The housing includes a plurality of breather openings 51 in the sidewalls. The housing 50 contains a gas/smoke/vapor generating device 53 a fan 54 located in the housing 50 to pass air at least partially through the housing 50 and to entrain at least some of the gas/smoke/vapor, and an outlet 55 through which the gas/smoke/vapor can pass prior to passing through (along) the perforated tube 52.

The housing 50 is typically connected to a power source (not illustrated) and provided with a control system to control the gas/smoke/vapor generating device 53 and the fan 54. A circuit board 56 for the control system is provided within the housing 50, with a control panel 60 with display 61 on the exterior of the housing 50 with which to adjust and/or program the control system.

Locating the fan 54 within the enclosure forms a pressure differential between the interior of the housing 50 and the exterior of the housing 50 with the fan 54 directing the gas/smoke/vapor and air into the outlet 55 and perforated tube 52, thus preventing or minimizing the amount of gas/smoke/vapor which can escape through the breather openings 51 in the housing 50. Power is provided to the device through a connection 62 to a power source.

The gas/smoke/vapor generating device according to this illustrated embodiment includes a reservoir 57 with a vaporizer 58 provided as the lid (cap or closure) for the reservoir 57. Normally, the reservoir 57 and vaporizer 58 are provided as a closed unit with a minimal number of openings. A door 63 is provided for removal and replacement of the reservoir 57.

The vaporizer 58 is provided with an outlet which is located adjacent the fan 54. Thus, in use the vaporized material (gas/smoke/vapor) will either disperse within the housing 50 and be entrained by the air drawn in through the breather openings 51 when the fan 54 is operational or the air drawn into the housing 50 by the fan 54 will more directly entrain the vaporized material as both flow towards the fan 54.

The fan 54 is provided with a fan housing 59 with the fan housing 59 located within the housing 50. The fan housing 59 includes a first annular portion in which the fan itself is located and a second, directing portion which communicates with the annular portion and links the annular portion with the outlet from the housing. According to the illustrated embodiment, the fan 54 and fan housing 59 are located on a rear wall of the housing 50, above and slightly behind the reservoir 57. As the material within the reservoir 57 is converted into gas/smoke/vapor, the gaseous material will normally rise, and thereby be entrained by the air entering through the breather openings 51 in the housing 50.

According to the illustrated preferred embodiment, the vaporizer 58 is spaced from the lower wall of the housing 50 with the breather openings 51 located at a similar level to the vaporizer 58 to promote the proper flow of air (and air entrained gas/smoke/vapor) to the outlet 55.

It should be appreciated that various other changes and modifications can be made to any embodiment described without departing from the spirit and scope of the invention.

The invention claimed is:

1. An apparatus comprising:
   a first enclosure containing a gas/smoke/vapor generating device;
   at least one inlet to allow air to pass into the first enclosure;
   a first enclosure outlet to allow air to pass out of the first enclosure;
   a second enclosure separated from the first enclosure by a partition; and
   a fan located in a fan enclosure,
      wherein the fan enclosure is located within the second enclosure and is provided with an inlet, the fan enclosure inlet comprising an opening in the partition and wherein the first enclosure outlet is in connection with the fan enclosure inlet, and
      wherein an outlet of the fan enclosure comprises a tapering enclosed portion which tapers towards an outlet in a wall of the second enclosure;
   whereby the fan causes air to pass from the at least one inlet through the first enclosure, the fan enclosure and fan outlet, the air at least partially entraining smoke/gas/vapors emitted from the smoke/gas/vapor generating device.

2. The apparatus of claim 1, comprising a flexible hose operatively associated with the fan enclosure outlet, the flexible hose containing at least one opening.

3. The apparatus of claim 2, wherein the hose has a multiplicity of perforations.

4. The apparatus as claimed in claim 1, wherein the first enclosure is provided with a door.

5. The apparatus as claimed in claim 1 wherein a plurality of inlets is provided as breather openings in walls of the first enclosure.

6. The apparatus as claimed in claim 1, comprising a shroud extending about the fan.

7. The apparatus as claimed in claim 1, wherein a wall of the apparatus is provided with a power socket to allow an electrical power supply to power the fan.

8. The apparatus as claimed in claim 1, wherein the first enclosure is provided with a power socket to allow a plug-in vaporizer to plug into the power socket.

9. The apparatus as claimed in claim 1, wherein a mosquito coil is placed in the first enclosure.

10. The apparatus as claimed in claim 1, wherein a mosquito candle is placed in the first enclosure.

11. The apparatus as claimed in claim 1, wherein a deodorizing agent is placed in the first enclosure.

12. The apparatus as claimed in claim 1, wherein a fragrance emitting agent is placed in the first enclosure.

13. An apparatus comprising:
   a first enclosure containing a gas/smoke/vapor generating device;
   at least one inlet to allow air to pass into the first enclosure;
   a first enclosure outlet in connection with a venturi to allow air to pass out of the first enclosure;
   a second enclosure separated from the first enclosure by a partition;
   a fan located in a fan housing,
      wherein the fan housing is located within the second enclosure and is provided with an outlet extending through the partition and through which pressurized air passes into one end of the venturi associated with the first enclosure outlet;
   whereby the fan causes air to pass from the exterior of the apparatus, through the fan housing, fan outlet, and venturi, sucking the air which has entrained therein smoke/gas/vapors emitted from the smoke/gas/vapor generating device.

14. The apparatus of claim 13, comprising a flexible hose operatively associated with the first enclosure outlet, the flexible hose containing at least one opening.

15. The apparatus of claim 14, wherein the hose has a multiplicity of perforations.

16. The apparatus as claimed in claim 13, wherein a deodorizing agent is placed in the first enclosure.

17. The apparatus as claimed in claim 13, wherein a fragrance emitting agent is placed in the first enclosure.

18. The apparatus as claimed in claim 13, wherein an insect repellant material is placed in the first enclosure.

* * * * *